United States Patent
Kawaji et al.

(10) Patent No.: US 6,177,098 B1
(45) Date of Patent: Jan. 23, 2001

(54) PATCH PREPARATIONS FOR PERCUTANEOUS ABSORPTION

(75) Inventors: Toshikuni Kawaji; Masahiro Yamaji, both of Kagawa (JP)

(73) Assignee: Teikoku Seiyaku Co., Ltd., Kagawa (JP)

(*) Notice: Under 35 U.S.C. 154(b), the term of this patent shall be extended for 0 days.

(21) Appl. No.: 09/214,762

(22) PCT Filed: May 11, 1998

(86) PCT No.: PCT/JP98/02063
§ 371 Date: Jun. 23, 1999
§ 102(e) Date: Jun. 23, 1999

(87) PCT Pub. No.: WO98/51288
PCT Pub. Date: Nov. 19, 1998

(30) Foreign Application Priority Data

May 12, 1997 (JP) .................................................. 9-135752

(51) Int. Cl.[7] .............................. A61F 13/00; A61F 13/02
(52) U.S. Cl. .......................... 424/443; 424/448; 424/449
(58) Field of Search .................................. 424/449, 447, 424/448, 443

(56) References Cited

U.S. PATENT DOCUMENTS

| 5,419,912 | * | 5/1995 | Morimoto et al. | 424/443 |
| 5,683,710 | * | 11/1997 | Akemi et al. | 424/448 |
| 5,773,028 | * | 6/1998 | Inagi et al. | 424/487 |
| 5,876,745 | * | 3/1999 | Muraoka et al. | 424/448 |

* cited by examiner

Primary Examiner—Thurman K. Page
Assistant Examiner—Susan Tran
(74) Attorney, Agent, or Firm—Evenson, McKeown, Edwards & Lenahan, P.L.L.C.

(57) ABSTRACT

Patch preparations for percutaneous adsorption with the use of supports showing appropriate strength as a patch support, which are excellent in drug barrier characteristics, compatibility with the skin, ODT effects and handling characteristics and can sustain these specific properties in a stable state over a prolonged period of time, thus ensuring good percutaneous absorption of drugs. In these patch preparation, use is made as the support of polyester film/nonwoven vinylon fabric laminates showing an elongation percentage of at least 5% and a tensile cutting load of at least 0.5 kg/10 mm, when measured by the test method specified in JIS K6732. In particular, the thickness of the polyester film constituting the laminate supports ranges from 1.5 to 6.0 μm and the unit weight of the nonwoven vinylon fabric ranges from 3 to 12 g/m$^2$.

11 Claims, 2 Drawing Sheets

PATCH PREPARATIONS FOR PERCUTANEOUS ABSORPTION

TECHNICAL FIELD

This invention relates to plasters for percutaneous absorption, using the laminated backing of polyester film and non-woven fabric of vinylon with the appropriate strength as a support of the plaster, more specifically, to the plaster in which an adhesive base material containing an active ingredient as being applied on the non-woven fabric of vinylon side of the laminated backing.

Even more specifically, the present invention relates to the plaster for percutaneous absorption using the laminated backing which is composed of polyester film and non-woven fabric of vinylon, and the opposite side of laminated polyester film with non-woven fabric pasted to is emboss treated. Furthermore, by using the laminated backing having elasticity ratio of more than 5%, and pulling severance weight of more than 0.5 kg/10 mm under JIS (Japan Industrial Standard)-K6732 testing method, the plasters of the present invention may have elasticity, may be easy to handle, and possesses the stable releasing of the active ingredient for the long period of time.

BACKGROUND ART

The backing for the conventional plasters for percutaneous absorption may be polyvinyl chloride film; olefin films such as polyethylene and polypropylene; polyurethane film; polyester/polyethylene-vinyl acetate copolymer (EVA) laminated film; EVA/non-woven fabric (rayon) laminated film or non-woven fabric of polyester/polyester laminated film, and these are very thin.

These backings except for polyester/EVA laminated film are used to produce the plaster for the active ingredient having systemic effect such as isosorbide dinitarate and amyl nitrite which possess the characteristic of sublimation and fugacity. However, there are same cases that the active ingredient in the adhesive base material is absorbed by the backing, and diffused from the adhesive base material. Therefore, the plasters have to be stored in sealed condition. However, during the storage, the active ingredient contained in the adhesive base material may decrease by diffusing and absorbed to the container. As a result, the stable drug releasing from the adhesive layer may not be obtained.

On the other hand, to prevent diffusion and absorption of the active ingredient to the backing, the polyester/EVA laminated film can be used to the backing of the plasters. However, because the close, adhesion to the skin is expected, the plaster must be laminated in thin layered composition preferably having thickness from 15 to 40 $\mu$m. Therefore, the plaster using the polyester/EVA laminated film as backing has same problems of the curl caused by static electricity and internal stress when applied to the skin.

To overcome these disadvantages, it has been proposed to use the backing which is laminated with polyester film and non-woven fabric of polyester (Japanese Patent Publication No. Hei 5-309128). Nevertheless, even in the case of using the proposed backing, there are still same disadvantages. For example, in the case of containing the oily absorption accelerant, such as oleic acid, isopropyl myristate or crotamiton in the adhesive base material, these oily substance may be absorbed to the non-woven fabric of polyester. Therefore, the releasing capability of the active ingredient from the adhesive base material decreases as the time passes by. Additionally, the plaster may be torn when the polyester film is thin (i.e. less than 1.5 $\mu$m), and the unit weight of non-woven fabric of polyester is less than 6 g/m$^2$. As a result, the backing for the plaster satisfied all expectations has not been available.

DISCLOSURE OF THE INVENTION

The inventors of the present invention had made intensive studies to overcome above-mentioned problems, and succeeded to discover the present invention. That is, the present inventors found out that the plasters for percutaneous absorption using a backing composed by non-woven fabric of vinylon pasted together with polyester film (laminated structured backing) possesses the excellent elasticity, easy handling, and the stable releasing of the active ingredient over the long period of time.

Therefore, the purpose of this invention is to provide the plasters for percutaneous absorption using a laminated backing of polyester film and non-woven fabric of vinylon with the appropriate strength as a support of the plaster.

One aspect of the present invention is to provide the plasters for percutaneous absorption using the laminated backing which is composed of polyester film and non-woven fabric of vinylon, having elasticity ratio of more than 5%, and pulling severance weight of more than 0.5 kg/10 mm under JIS-K6732 testing method.

In above condition, this invention provides the plasters for percutaneous absorption with the thickness of the polyester film of the laminated backing being 1.5–6.0 $\mu$m, more preferably 2.0–3.5 $\mu$m, and the unit weight of the non-woven fabric of vinylon being 3–12 g/m$^2$, more preferably 6–8 g/m$^2$.

Therefore, the most preferred embodiment of the present invention is to provide the plasters for percutaneous absorption using polyester/non-woven fabric of vinylon laminated backing with the elasticity ratio of more than 5%, and pulling severance weight of more than 0.5 kg/10 mm under JIS-K6732 testing method, and said polyester film having the thickness of 1.5–6.0 $\mu$m, more preferably 2.0–3.5 $\mu$m, and said non-woven fabric of vinylon with the unit weight of 3–12 g/m$^2$, more preferably 6–8 g/m$^2$.

Furthermore, in the preferred embodiment, this invention provides the plaster for percutaneous absorption using the laminated backing of polyester film and non-woven fabric of vinylon in which the opposite side of laminated polyester film with non-woven fabric pasted to is emboss treated.

Therefore, in the another embodiment, this invention provides the plaster for percutaneous absorption which comprising the adhesive base material containing the active ingredient spread onto the non-woven fabric side of the above-mentioned laminated backing.

The plaster for percutaneous absorption using the backing comprising of polyester film/non-woven fabric of vinylon, and the adhesive base material containing the active ingredient spread onto the said backing shows excellent performance. That is, barrier ability of the active ingredient contained in the base material, close adhesion to the skin, occlusive dressing technique (ODT) effect, and easy handling. Furthermore, these features are kept stable for long time period. Thus the plasters of the present invention may be the excellent transdermal preparation for the various kinds of medicine.

BEST MODE FOR CARRYING OUT THE INVENTION

Figure 1:
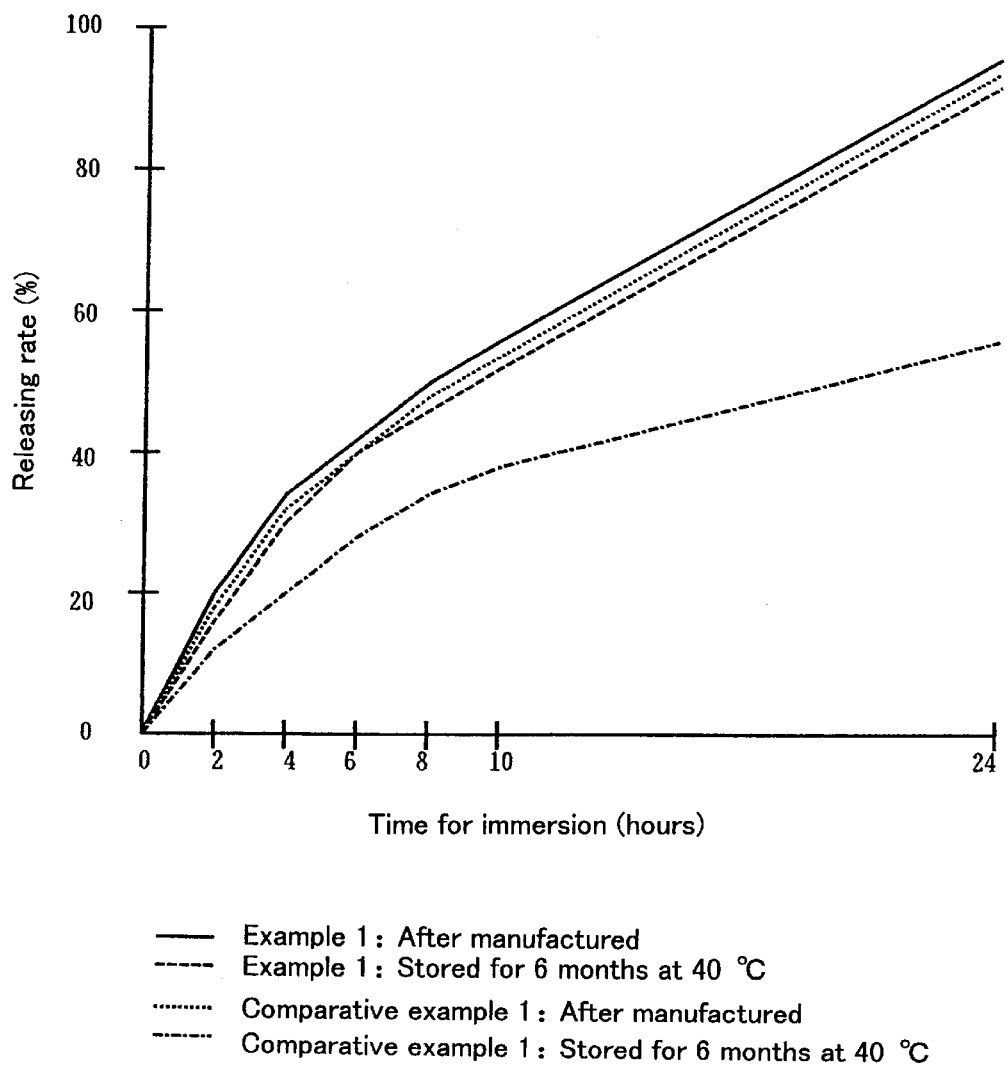
FIG. 1 shows the results of the Test I, that is, storage stability test (drug releasing test) on the plasters of the present invention.

The features and distinctive strength of the various kinds of film and non-woven fabric composing the backing for the plasters of the present invention is described to explain the present invention in more detail.

The non-woven fabric of vinylon used for the laminated backing of the plasters of the present invention is made from polyvinyl alcohol fiber which is oil, organic solvent, and gas barrier resistant, and also is electrified resistant. It is found that the laminated backing (laminated film) consisting of non-woven fabric using above-mentioned fiber and the polyester film is excellent to be used as a support for the plasters for percutaneous absorption.

In general, the plasters for percutaneous absorption containing the active ingredient which show the systemic effect, may be usually applied to the regions of chest, abdominal, dorsal, and the lower leg. The skin in these regions has little flexibility, and therefore, the plasters to be applied to these regions may not be required flexibility; however, elasticity of the plaster has to be required.

Therefore, it is preferred to use very thin polyester film in case of using it to prevent diffusion of the drug. However, to keep the good handling condition, the laminated backing of polyester film and non-woven fabric of vinylon, the film and the non-woven fabric themselves are preferred to have appropriate thickness. Namely, in the case of the film and the non-woven fabric being too thin, the resulting laminated backing may be torn at the time of exfoliation after the application, and is not favored.

Accordingly, for the suitable backing of the present plasters, it was found that the laminated backing of polyester film and non-woven fabric of vinylon ought to have the elasticity rate of more than 5%, and the pulling severance weight of more than 0.5 kg/10 mm under JIS-K6732 testing method.

It is not preferred to use the backing with the elasticity rate less than 5% because even in the case of high elasticity of the backing not being required, such backing gives uncomfortable feeling at the time of application on the skin. Also the backing with the pulling severance rate being less than 0.5 kg/10 mm is not preferred because the plaster is probable to be torn.

The polyester film used for the laminated backing of the plaster of the present invention may have thickness of 1.5–6.0 μm, more preferably 2.0–3.5 μm to prevent diffusion of the drug, keeping ODT effect and elasticity, and to this end, the saturated polyester can be used. Such a polyester film may be the one composed mainly by polyethylene terephtalate, in the view points of safety on the living body, practicality and the wide usability.

The non-woven fabric of vinylon used for the laminated backing of the plasters of the present invention may have weight of 3–12 g/m$^2$, more preferably 6–8 g/m$^2$. The non-woven fabric of vinylon may be produced from vinylon fibers by pasting with the binder or by tangling with the machine. It is also possible to produce the non-woven fabric without using the binder; however, the resulting non-woven fabric may have low mechanical strength. Therefore, in the case of using the thin non-woven fabric for the laminated backing of the present invention, the fabric requires the appropriate strength, and it is preferred to use the binder for the production of the thin non-woven fabric.

Accordingly, in a preferred specific embodiment, the present invention is to provide the plasters for percutaneous absorption using the laminated backing of polyester film/non-woven fabric of vinylon, in which the elasticity rate being more than 5%, and severance rate being more than 0.5 kg/10 mm under the JIS-K6732 testing method, and the thickness of said polyester film being 1.5–6.0 μm, more preferably 2.0–3.5 μm, and furthermore, unit weight of the non-woven fabric of vinylon being 3–12 g/m$^2$, more preferably 6–8 g/m$^2$.

The laminated backing used for the plasters of the present invention may be produced with polyester film and non-woven fabric pasted together by using the conventional binder, such as polyester type or acrylic type binder, with the weight of 1–5 g/m$^2$ after drying.

The polyester film, in general, has the glassy finished surface and reflects the outside light when applied to the skin. This lustrous cause the plaster to be seen low in quality. Therefore, to gain high quality look for the plaster, the surface of the polyester film preferably be processed with emboss treatment. Such a emboss treatment may shape for example, leather type, diamond type or silky type pattern so as to change lustrous surface to the grinding type, and it is better in looks and the feeling when applied to the skin. However, the depth of emboss treatment has to be controlled as not to torn the plaster at the time of exfoliation, since the laminated backing becomes uneven in its thickness.

The plasters for percutaneous absorption of the present invention may be manufactured by spreading the adhesive base material containing the active ingredient onto the non-woven fabric side of the laminated backing.

The active ingredients to be used for the plasters of the present invention may not be limited. Any transdermal absorbable drugs expected local or systemic effect may be used for the plasters of the present invention. Such drugs may be for example, depressor, diuretic, anti-asthmatic, male and/or female hormone, tranquilizer, sedative, anesthesia, antibacterial, coronary vasodilator, antiemetic and so on. These drugs can be used in combination with more than two kinds in the plasters of the present invention.

The adhesive base material used for the plasters of the present invention may be any one of the biologically acceptable adhesive bases, such as acrylic acid type base, synthetic rubber, natural rubber, silicon rubber and so on. Such acrylic acid type base may be produced from 2-ethylhexyl acrylate monomer as main component with a monomer by polymerization reaction or cross-linking reaction. Such a monomer may be methyl acrylate, ethyl acrylate, hydroxyethyl acrylate, 2-hydroxyethyl methaccrylate, acrylic acid, vinyl accetate or N-methyl-2-pyrrolidene. The polymerization reaction initiator may be azobisisobutyronitrile or benzoyl peroxide, and the cross-linking agent may be toluene diisocyanate or hexamethylene diisocyanate.

Furthermore, the natural or synthetic rubber type adhesive bases may be produced from elastomers such as natural rubber, isoprene rubber, styrene-butadiene rubber, polyisobutylene, styrene-isoprene-styrene block copolymer, by adding tackifier, antioxidants, softeners and oils adjusting the amount of these components to obtain the desired properties of the adhesive bases. The tackifier may be resins such as rosin type, ester gum type or petroleum resin, and the antioxidants may be dibutylhidoroxytoluene or pentaerythrityl-tetrakis[3-(3,5-t-butyl-4-hydroxyphenyl)] propionate.

The softeners may be liquid paraffin or liquid rubber such as polybutene or polyisoprene, and oils may be liquid paraffin or petrolatum.

The silicon type adhesive prepared from silicon rubber and silicon resin by using peroxide; or methyl or methylphenyl type tackifier prepared by additional reaction may also be used.

EXAMPLES

The present invention will be further illustrated by the following examples. It is to be understood that the present invention is not limited to these examples.

Example 1

27.5% by weight of styrene-isoprene-styrene block copolymer (Kuraprene TR-1107/JSRshellelastomer), 41% by weight of hydrogenated rosin resin (KE-311/Arakawa Chemical Industry Inc.), 10% by weight of liquid rubber (LIR-50/Kuraray), 0.5% by weight of dibutylyl hydroxytoluene (BHT "Takeda"/Takeda Chemical Industries, Ltd.), and 1% by weight of oleic acid ("JSCI"oleic acid/ NOF Co.) were dissolved in toluene (grade: JSCI). Then, to this mixture was added 20% by weight of isosorbide dinitrate solution (20% by weight of isosorbide dinitrate "Chuka"/ Chugoku Kayaku Co.) to obtain the adhesive base solution. The resulting adhesive base was spread onto one side of the polyester liner in which both sides are silicon treated so as the dry weight of base to be 50 g/m$^2$. After drying for 10 minutes at about 80° C., this polyester film was layered with the laminated backing of polyethylene terephthalate film (thickness: 3.5 μ) and 8 g/m$^2$ of non-woven fabric of vinylon. The resultant was cut into desired size to produce the plaster of the present invention.

The pulling severance weight of the laminated backing of polyethylene terephtahlate/non-woven fabric of vinylon used for this example was 1.7 kg/10 mm for the length, and 1.2 kg/10 mm for width, and the elasticity is 13% for the length and 20% for the width.

Example 2

To 40% by weight of acrylic acid type adhesive base composed from 85% by weight of 2-ethylhexyl acrylate and 15% by weight of N-methyl-2-pyrrolidone in ethyl acetate solution (222.5 g) was added 6 g of 17 β-estradiol in N,N'-dimethylacetamide solution (12 g), and the mixture was stirred. Then, 5 g of oleic acid and 5 g of crotamiton were added to this mixture, and the resultant mixture was stirred to produce the adhesive base. The adhesive base thus obtained was spread onto the silicon treated polyester film (thickness: 75 μm) using doctor's blade so as the thickness of the base to be 50 μm after drying. The resultant was dried for 10 minutes at about 80° C. to remove off the solvent, and then layered with the laminated backing of polyester film (thickness: 3.5 μm) and 8 g/m$^2$ of non-woven fabric of vinylon. The resultant was then cut into desired size to produce the plaster containing estradiol of the present invention.

The pulling severance weight of the laminated backing of polyester/non-woven fabric of vinylon used for this example was 1.5 kg/10 mm for the length, and 1.0 kg/10 mm for width, and the elasticity was 5.5% for the length and 10% for the width.

Example 3

20% by weight of styrene-isoprene-styrene block copolymer, 50% by weight of super light colored rosin resin, 18% by weight of polybutene, 2% by weight of liquid paraffin and 1% by weight of dibutylhydroxytoluene were fused and kneaded to each other in the kneader at about 150° C., then the mixture was cooled to about 120° C. On the other hand, 5% by weight of crotamitone, 1% by weight of diphenhydramine, 2% by weight of lidocaine, and 1% by weight of isopropyl methylphenol were dissolved at about 60° C., and this solution was added to the above mixture in the kneader. Then, the resulting mixture was further kneaded to produce the adhesive base. The warm adhesive base thus obtained was spread onto the silicon treated polyester film (thickness: 75 μm) to be the thickness of base of 100 μm. The resultant was then cooled and layered with the laminated backing of polyester film (3.5 μm) and 12 g/m$^2$ of non-woven fabric of vinylon. The laminated product thus obtained was then cut into the desired size to produce the plaster of the present invention for antipruritic.

The pulling severance weight of the laminated backing of polyester/non-woven fabric of vinylon used for this example was 0.8 kg/10 mm for the length, and 0.5 kg/10 mm for the width, and the elasticity was 16% for the length and 24% for the width.

Comparative Example 1

The plaster of the Comparative Example 1 was produced in the substantially same manner as described in Example 1. In the Comparative Example 1, non-woven fabric of polyester was used for the laminated backing instead of non-woven fabric of vinylon.

Testing Examples

To demonstrate the usefulness of the plasters for percutaneous absorption of the present invention, the storage stability test and in vitro skin permeability test were conducted comparison to the plaster obtained in the Comparative Example.

Test 1: Storage Stability Test:

The each plaster produced in the Example 1 and the Comparative Example 1 is placed in the bag composed of aluminum and polyethylene, and stored under 25° C. and 40° C. temperature condition. After stored for the determined period of time, the releasing amount of the active ingredient (isosorbide dinitrate) form each plaster was determined in accordance with the Method No. 2 of "Dissolution Tests" stated in the *Japanese Pharmacopoeia* (12th amendment).

The releasing amount of isosorbide dinitrate in the solvent was measured with the passage of time by HPLC. The results are shown in the FIG. 1.

In the figure, the drug releasing rates from the samples of the plaster in the Example 1 and the Comparative Example 1 are shown in time series. The plaster just after manufactured and the plaster stored for 6 months under the 40° C. temperature condition were used for the test samples.

As it is clearly shown in the results in the figure, the releasing rate of drug from the adhesive base of the plaster of the present invention does not change even after the long storage period compared with the plaster just after manufactured. However, the releasing rate from the adhesive base of the plaster of the Comparative Example was decreased in comparison with the plasters of the present invention.

As a result, it can be understood that the plasters for percutaneous absorption of the present invention are stable for long time of period.

Test 2: In Vitro Skin Permeability Test on rats

The abdominal region of Wistar strain rats (male, 6–7 weeks old) was shaved with a hair dipper and a shaver, and the skin was taken out. The obtained skin was placed in the Frantz-type diffusion cell, and the each plaster of the Example 1 and the Comparative Example 1, cut into 25 mm in diameter (as it was equal to 4.91 mg of isosorbide dinitrate), were applied on the skin. The physiological saline solution was filled in the receptor side of the cell, and the warm water of about 37° C. was circulated through the cell jacket.

The samples were taken out as the time series, and the amount of isosorbide dinitrate permeated the skin was measured by the HPLC method.

The plaster just after manufactured and the plaster stored for 6 months under the 40° C. temperature condition were used for the test samples.

Figure 2:
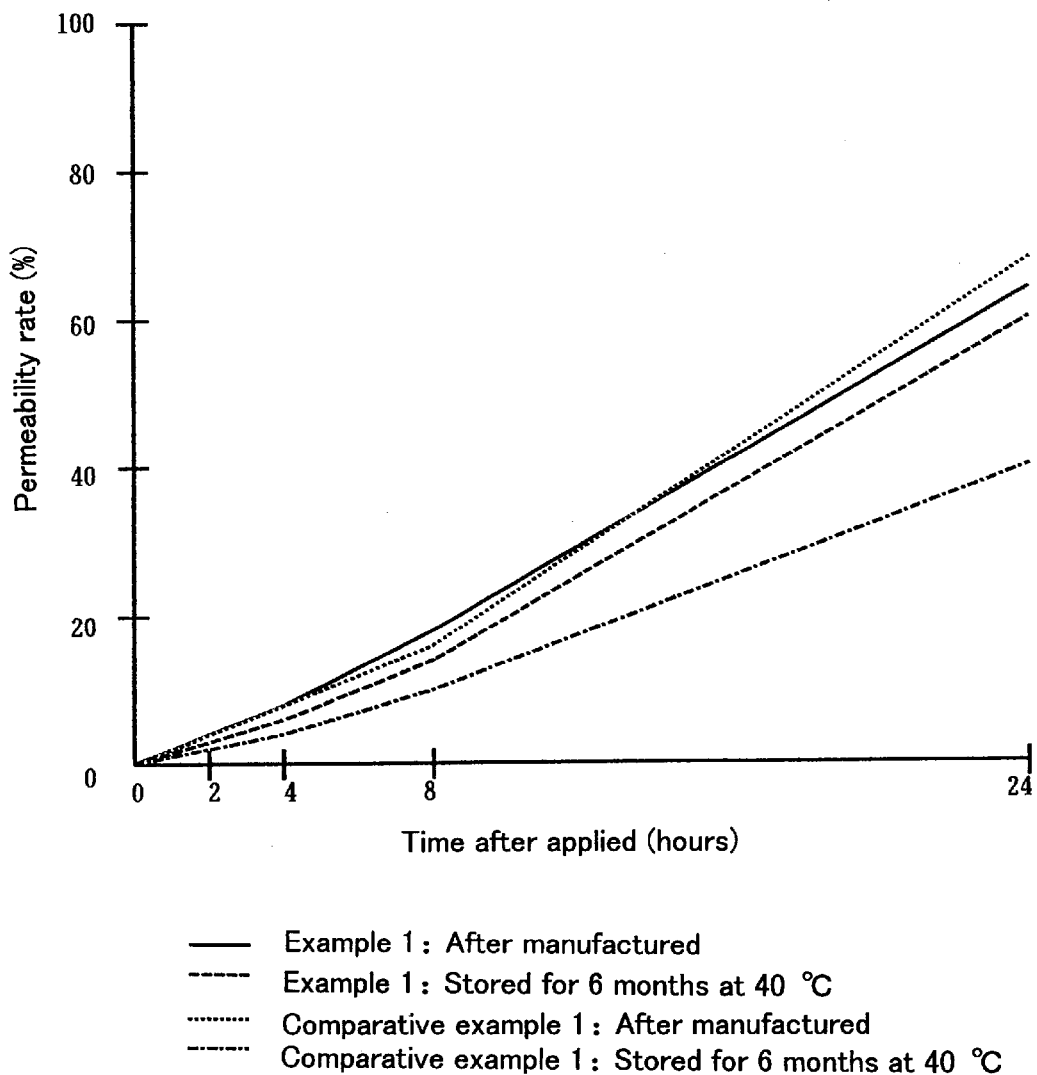
FIG. 2 shows the results of the Test II, that is, in vitro skin permeability test using rat skin on the plaster of the present invention.

The results are shown in the FIG. 2.

As it is clearly shown in the results in the figure, the amount of isosorbide dinitrate permeated the skin from the adhesive base of the plaster of the present invention does not change even after the long storage period compared with the just after manufactured. However, permeability of isosorbide dinitrate of the plaster of the Comparative Example is decreased in comparison with the plasters of the present invention.

As a result, it can be understood that the plasters for percutaneous absorption of the present invention possesses the stable permeability of the drug for long time of period, and also it is excellent in close adhesion to the skin.

INDUSTRY APPLICABILITY

According to the present invention, there can be provided the plasters for percutaneous absorption using the laminated backing of polyester film and non-woven fabric of vinylon. The laminated backing used for the plasters of the present invention is very elastic and excellent in handling, and also possesses the stable releasing of the active ingredient from the adhesive base for long period of time. Especially it is excellent in the barrier effect of the drug, close adhesion to skin, the ODT effect, and easy handling and these features are stable for long period of time.

Accordingly, this invention provides the plasters for percutaneous absorption, which would be appropriate to be applied for the long time period, and thus excellent in the medical result.

What is claimed is:

1. A plaster for percutaneous absorption which comprises a laminated backing comprising a polyester film/non-woven fabric of vinylon having an elasticity rate of more than 5% and severance rate of more than 0.5 kg/10 mm "said polyester film has a thickness of 1.5–6.0 $\mu$m, and the unit weight of the vinylon non-woven cloth is 3–12 g/m$^2$".

2. The plaster claimed in claim 1, wherein the laminated backing comprises a polyester film having a thickness of 1.5–6.0 $\mu$m and non-woven fabric of vinylon having a unit weight of 3–12 g/m$^2$, and said laminated backing having an elasticity rate of more than 5% and severance rate of more than 0.5 kg/10 mm.

3. The plaster claimed in claim 1, in which the side of the polyester film on which the non-woven fabric is laminated is embossed.

4. The plaster claimed in claim 1, further comprising an adhesive base containing an active ingredient layered to the non-woven fabric.

5. The plaster claimed in claim 1, in which the side of the polyester film on which the non-woven fabric is laminated is embossed.

6. The plaster claimed in claims 2, in which the side of the polyester film on which the non-woven fabric is laminated is embossed.

7. The plaster claimed in claim 1, further comprising an adhesive base containing an active ingredient layered to the non-woven fabric.

8. The plaster claimed in claims 2, further comprising an adhesive base containing an active ingredient layered to the non-woven fabric.

9. The plaster claimed in claim 4, wherein the active ingredient is isosorbide dinitrate or amyl nitride.

10. The plaster claimed in claim 4, wherein the active ingredient is isosorbide dinatrate or amyl nitride.

11. The plaster claimed in claims 8, wherein the active ingredient is isosorbide dinatrate or amyl nitride.

* * * * *